United States Patent [19]

Solazzi

[11] Patent Number: 4,698,210
[45] Date of Patent: Oct. 6, 1987

[54] SAMPLE CUP APPARATUS FOR USE IN X-RAY SPECTROSCOPY EMPLOYING SELECTIVELY OPERATED VENTING MEANS

[75] Inventor: Michael C. Solazzi, Eastchester, N.Y.

[73] Assignee: Chemplex Industries, Inc., Eastchester, N.Y.

[21] Appl. No.: 676,833

[22] Filed: Nov. 30, 1984

[51] Int. Cl.$^4$ .................... G01N 23/10; G01N 23/20; G01N 23/223; G01N 21/51

[52] U.S. Cl. .................... 422/102; 250/428; 378/45; 378/49; 378/79; 356/246

[58] Field of Search .................... 422/102; D24/2, 29; 73/864.91; 250/428; 356/246; 220/368, 373, 374; 378/79, 82, 83

[56] References Cited

U.S. PATENT DOCUMENTS

| | | | |
|---|---|---|---|
| 238,693 | 2/1976 | Solazzi | D24/29 X |
| 2,144,255 | 1/1939 | Carpenter | 422/102 X |
| 4,037,109 | 7/1977 | Hosokawa et al. | 378/79 X |
| 4,046,138 | 9/1977 | Libman et al. | 73/864.91 X |
| 4,346,299 | 8/1982 | Mitteldorf et al. | 422/102 X |
| 4,409,854 | 10/1983 | Solazzi | 250/428 X |
| 4,448,311 | 5/1984 | Houser | 356/246 X |
| 4,575,869 | 3/1986 | Torrisi et al. | 356/246 X |

Primary Examiner—Michael S. Marcus
Assistant Examiner—Lynn M. Kummert
Attorney, Agent, or Firm—Arthur L. Plevy

[57] ABSTRACT

A sample cup for use in spectroscopy consists of a cap member having an extending peripheral flange about a closed top surface, with a downwardly extending cylindrical bottom section, the peripheral flange of the cap member has a through aperture located on the inner edge of the flange and extending towards the periphery, a cell body is of a tubular configuration with an opened top and bottom with the opened top surrounded by a flange having an aperture on an inner surface for communicating with the internal hollow of the cell body. The cap member is adapted to coact with the opened top of the cell body and is rotatably supported thereon, whereby in a first mode the through aperture communicates with the cell aperture to create a vent passageway and in a second rotatable position, the apertures do not align to create a closed cell mode. The opened bottom of the cell body is covered by a thin plastic sheet which is held in position after a sample is placed in the hollow of the cell body by an annular retaining ring.

10 Claims, 6 Drawing Figures

SAMPLE CUP APPARATUS FOR USE IN X-RAY SPECTROSCOPY EMPLOYING SELECTIVELY OPERATED VENTING MEANS

BACKGROUND OF THE INVENTION

This invention relates to a sample cup for use in accommodating specimens for spectrochemical analysis in general and more particularly to such a cup including selectively operated venting means.

Technological advancements in both wavelength-dispersive (WD-XRF) and energy dispersive (ED-XRF) x-ray fluorescence instrumentation have furnished the spectroscopist the means to accommodate virtually all types of sample materials submitted for analysis.

In this technology sample cups are employed to hold or contain the liquid, solid and powdered specimens under normal atmospheric pressures, gas pressures or in vacuum for performing analysis on the contained sample using the above and other techniques.

As such, sample cups are well known. Many prior art sample cups consisted of three components as a cup-shaped cell having a closed bottom and an opened top, an annular collar and a snap-on ring used to hold a sheet of plastic after insertion of the sample and for closing the opened top prior to spectroanalysis. A typical prior art sample cup is shown in U.S. Pat. No. Des. 238,693 entitled CELL FOR X-RAY SPECTROSCOPY OR SIMILAR ARTICLE issued on Feb. 3, 1976 to Monte J. Solazzi.

Sample cups or cells are available in many different configurations such as those sold by Chemplex Industries of 140 Marbledale Road, Eastchester, NY 90707, the assignee herein.

Many sample cups require venting means whereby a hole or aperture is formed in a closed surface of the cup to enable the equalization of pressure.

The reasons a vent is required has been explained in great detail in the Background of the Invention as specified in U.S. Pat. No. 4,409,854 entitled SAMPLE CUP WITH VENTING MEANS FOR USE IN X-RAY SPECTROSCOPY issued on Oct. 18, 1983 to M. C. Solazzi and assigned to the assignee herein. In that patent there is described a sample cup which includes on the bottom surface of the cell an upstanding plunger positioned within a thinner area of the surface. The plunger has grooves directed from top to bottom on the side walls and when depressed ruptures the closed bottom of the cell to create the vent necessary to equalize the pressure.

Essentially, the formation of the vent as disclosed in the above noted patent as well as in other prior art devices causes a permanent rupture or breakage of the cell body, and hence once a vent passage is accommodated, the cell is permanently damaged as containing a permanent vent and therefore a closed cell condition cannot be obtained again.

It is an object of the present invention to provide an improved sample cup having selectively operated venting means whereby the cup can be vented in a first mode and then fully closed in a second mode and re-vented again and so on.

This is accomplished by means of a snap-on rotatable cap which coacts with a cylindrical cell body. Both the cap and the cell body possess corresponding venting apertures to enable alignment of the apertures in a venting mode and to close the cup when the apertures are out of alignment.

The structure of the cell eliminates the necessity of the user to form venting apertures by the use of a sharp tool or by employing other venting mechanisms of the prior art.

BRIEF DESCRIPTION OF THE PREFERRED EMBODIMENT

A selectively ventable sample cup for retaining a specimen to be subjected to spectrochemical analysis, comprising:
 a cell body of a cylindrical configuration having an opened top and an opened bottom, and having a peripheral flange about said opened top with an aperture on the inner periphery of said flange in communication with the internal hollow of said cell body,
 a rotatable cap member positioned over said opened top of said cell body and having a closed top surface surrounded by an extending peripheral flange, with an area of said flange containing a through aperture, with said flange of said cap member sitting on said flange of said cell body to enable said apertures to communicate in a first rotatable position to form a venting passageway from the hollow of said cell to the closed top surface of said cap and to close said passageway in a second rotatable position,
 means covering said opened bottom of said cell body when a specimen is contained within said hollow.

DETAILED DESCRIPTION OF THE FIGURES

Figure 1:
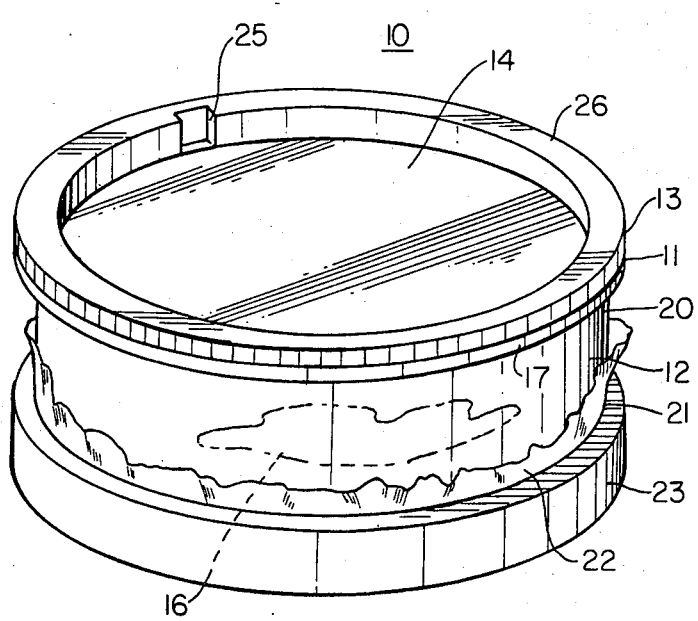
FIG. 1 is a perspective plan view of a sample cup according to this invention.

Referring to FIG. 1, there is shown a perspective plan view of an assembled sample cup 10 according to this invention.

Essentially, the cup 10 consists of three components. A top cylindrical member 11 constitutes a cap which as will be explained is rotatably mounted on the cell body 12. The cap 11 as shown has a peripheral flange 26 which has a knurled or grooved side surface 13 to facilitate turning of the same with respect to the cell body 12.

The peripheral flange 26 extends above and surrounds a closed central area 14 of the cap 11. This central area 14 as surrounded by the flange 26 serves as a reservoir for sample material 16 contained within the internal hollow of the sample cup 10. The reservoir thus formed collects heat sensitive liquid samples which may tend to expand as a result of heat generated by intense excitation during the analysis and such liquids may escape via the vent hole 25.

The cap 11 fits into the cell body 12 where the flange of the cap 11 sits on the flange 17 associated with the cell body 12. As will be explained, the cap is retained in the cell body by coacting ridges and indentations formed on each unit.

The cell body 12 has an opened top 20 and an opened bottom 21. The opened top 21 is covered by the cap. The sample 16 is introduced in the cell body via the opened top or bottom and the bottom is covered by a flexible sheet 22 of Mylar ® and held in place by an annular retaining ring 23, which snaps over the bottom peripheral side of the cell body 12.

In order to accomplish venting, the cap member has a venting aperture 25 which is a rectangular through aperture positioned on the inner surface of the flange 26 and extending vertically from top to bottom which directly communicates with the flange 17 of the cell body 12. The aperture 25 is rectangular but any other shape will suffice.

The flange 17 of the cell body has a corresponding rectangular aperture and as will be shown, when aligned with aperture 25, creates an unobstructed passageway from the interior of the cell body 12 via the aperture 25 on the cap 11. This vent passageway results when the aperture in the cap 11 is aligned with the aperture or vertical groove on the cell body 12. By rotation of the cap 11, the apertures are caused to be misaligned which condition converts the cell 10 to a closed unit. Hence venting is selectively achieved by rotation of the cap 11 with respect to the cell body to create a vent passageway in one mode and to close the passageway in another mode.

Figure 2:
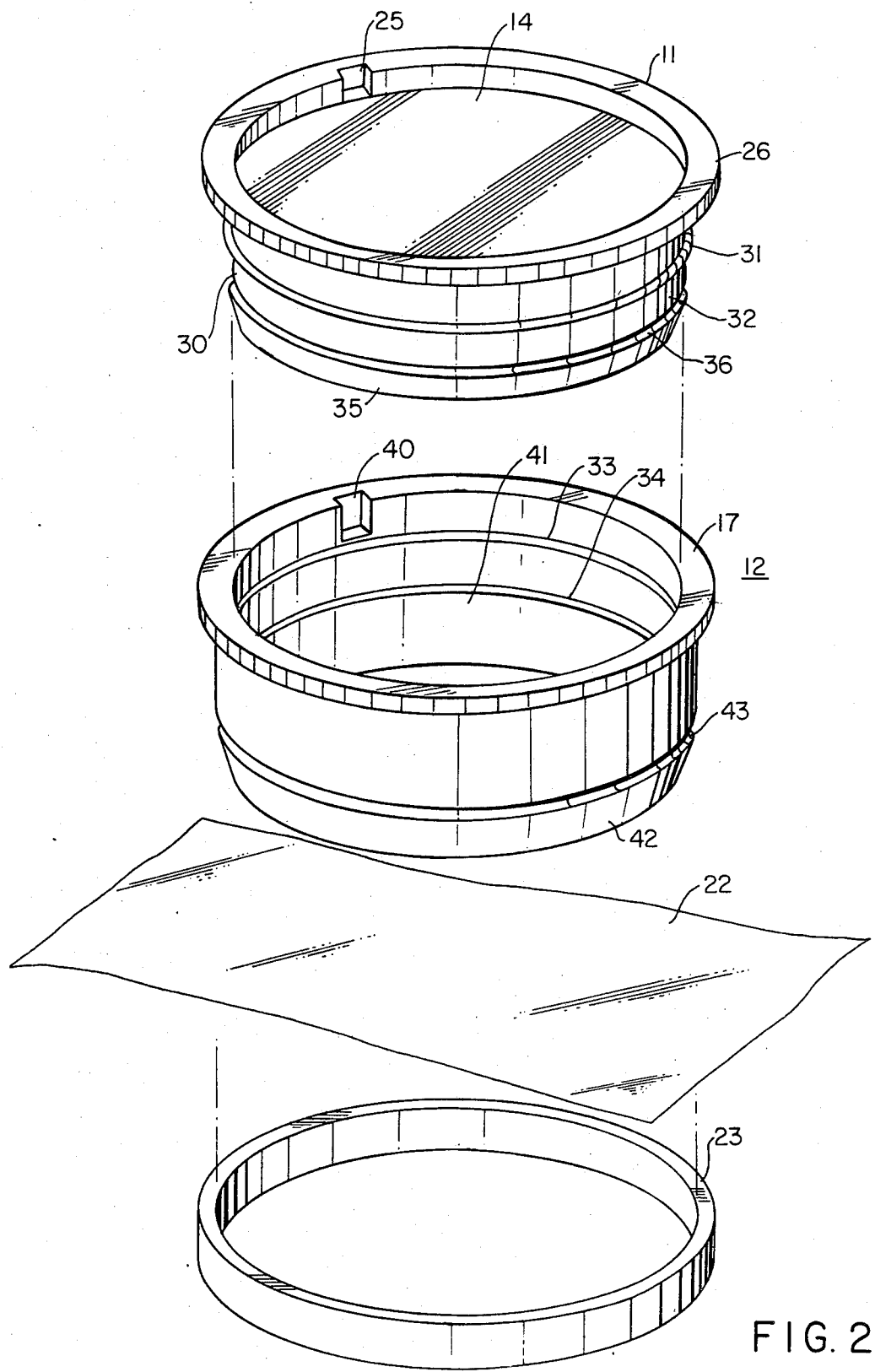
FIG. 2 is an assembly view of the cup of FIG. 1.

Referring to FIG. 2, there is shown a perspective assembly plan view depicting the rotatable cap 11, the cell body 12 and the snap-on ring 23 and plastic sheet 22.

As seen in FIG. 2, the cap 11 has a closed top surface 14 surrounded by the peripheral flange. The cap vent aperture 25 is depicted on the inner periphery of the flange. The cap 11 has a downwardly extending inner section 30 of a cylindrical configuration with the outer surface containing a peripheral ridge or bead 31 which coacts with a corresponding indentation 33 on the inner sidewall of the cell body 12. Located beneath the ridge 31 is a peripheral depression or indentation 36 which coacts with an inner peripheral ridge 34 on the inner surface of the cell body 12.

The bottom portion 35 of the section 32 is slightly tapered to allow for easy insertion of the cap 11 into the cell body 12. Thus the cap 11 can be snapped into the cell body 12 by means of the ridges as 31 and 34 coacting with the respective indentations 33 and 36. The cell body 12 has a top peripheral flange 17 which coacts with the peripheral flange 26 of the cap 11. An aperture 40 is positioned on the inner wall of the cell body 12 and extends into the flange area to enable communication with aperture 25 of the cap 11 when the cap 11 is rotated in position to cause alignment. This position creates a venting passageway for the sample cup 10.

The cell body 12 as indicated has an opened top 41 and an opened bottom 42. The cell body 12 is a longitudinal tubular member and has a ring accommodating indentation about the outer periphery nearer the bottom end 42. The area between the indentation 43 and the bottom end 42 is tapered to allow for easy insertion of the ring 23. As indicated, the Mylar ® sheet 22 is placed over the opened bottom 42 of the cell body 12 and held in place by the ring 23 after a sample or specimen is introduced into the hollow of the cup 10.

Figure 3:
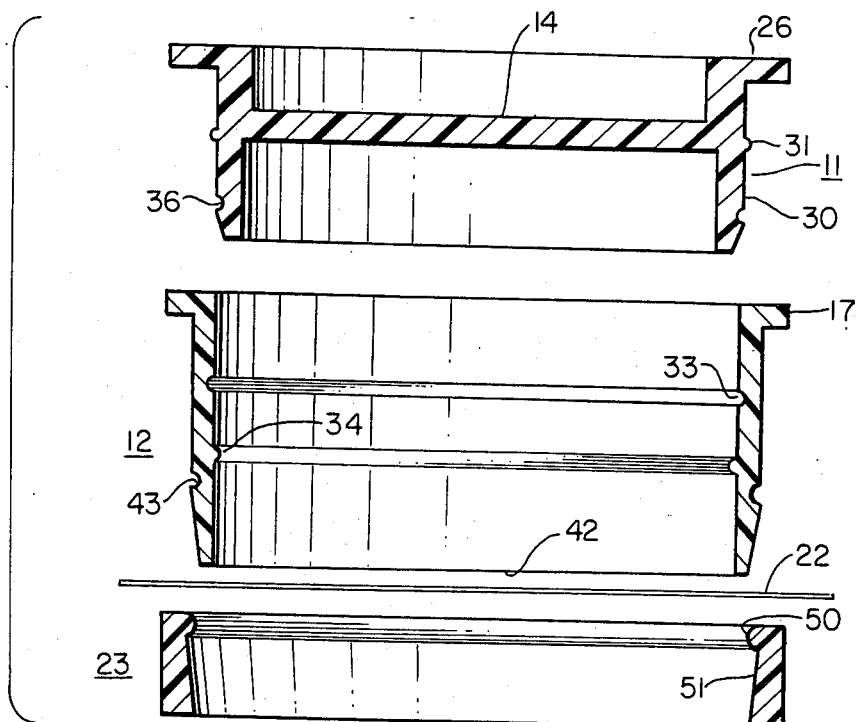
FIG. 3 is a cross sectional view of a sample cup assembly.

Referring to FIG. 3, there is shown the cap 11, the cell body 12 and the ring 23 in cross section for clarity. The same reference numerals have been retained to designate the respective parts of each unit in the sample cup assembly. As seen, the ring 23 has an internal ridge 50 which snaps into the indentation 43 of the cell body 12. The inner wall 51 of the ring tapered to match the taper of the cell body is located between the indentation 43 and the opened bottom 42.

Figure 4:
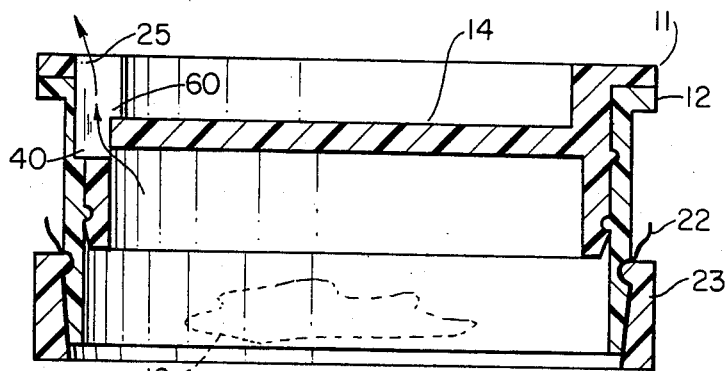
FIG. 4 is a cross sectional view of an assembled cup depicting an open vent mode.

As seen in FIG. 4, the cap 11 is rotated to cause aperture 25 to be aligned with aperture 40 to create a venting passageway 60.

Figure 5:
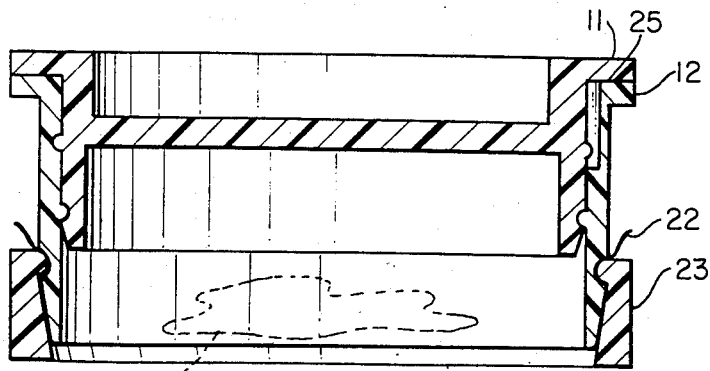
FIG. 5 is a cross sectional view of an assembled cup depicting a closed vent mode.

In FIG. 5, the cap 11 is rotated to cause the aperture 25 not be aligned with the venting passageway 60 and indicative of the closed mode.

Figure 6:
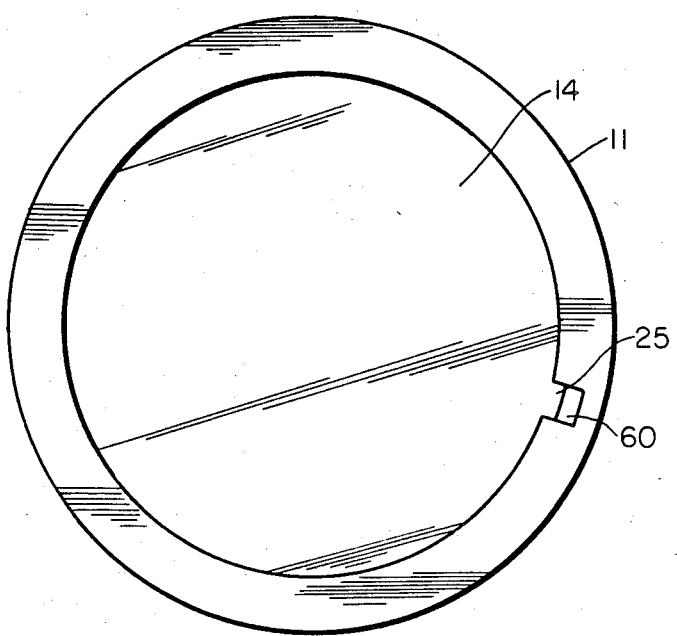
FIG. 6 is a top plan view of the sample cup.

In FIG. 6, there is shown a top view of the sample cup with the venting passageway 60 opened. As one can ascertain, by rotating the cap 11, the venting hole is then closed or opened as selectively desired.

The component parts of the cup 10 as the cap 11, the cell body 12 and the ring 23 are fabricated from a suitable plastic, preferably a thermoplastic such as polyethylene. This material exhibits resistance to chemical degradation, deterioration by excitation source exposure and thermal softening by x-ray bombardment. Other criteria include rigidity to prevent thin-film distortion, elasticity for ease in firmly securing thin-film sample supports without formation of pin holes and purity with particular regard to sulfur content.

In practice, the cap 11 is first inserted in place on the cell body 12. The cap 11 firmly snaps into place based on the above described coacting ridges and indentations. The cell is inverted and a liquid or powdered solid sample is introduced into the internal hollow of the cell. The thin film plastic sheet or support is then placed over the opened bottom end 42 of the cell and held in place by the ring 23. Prior to analysis, the cap 11 is rotated to the appropriate position for pressure equalization. The overflow reservoir 14 associated with the cap 11 collects heat-sensitive liquid samples which tend to expand due to the heat generated by intense radiation. The cup essentially has a 40 mm diameter and 23 mm in height. The aperture of the cell is 32 mm in diameter permitting a sample surface exposure area of 493 $mm^2$ for analytical investigation. The above dimensions are by way of example only as other values can be employed as well.

I claim:

1. A selectively ventable sample cup for retaining a specimen to be subjected to spectrochemical analysis, comprising, a cell body of a cylindrical configuration having an opened top and an opened bottom, and having a first peripheral flange about said opened top with an aperture means on an inner periphery of said first flange in communication with an internal hollow defined by said cell body, a rotatable cap member positioned over said opened top of said cell body, said rotatable cap member having a closed top surface and a peripherally disposed sidewall, wherein said top surface is surrounded by a second peripheral flange extending upwardly and outwardly therefrom, wherein said peripherally disposed sidewall is insertable within said opened top of said cell body, said second extending peripheral flange limiting the depth of penetration of said peripheral sidewall into said cell body, said closed top surface and said second upwardly and outwardly extending peripheral flange defining a reservoir for collecting liquid, said second flange having aperture means, with said second flange of said cap member sitting on said first flange of said cell body when said peripherally disposed sidewall is inserted within said open top to enable said aperture means of said first and said second flanges to communicate when said cap member is in a first rotatable position to form an interior venting passageway from the internal hollow of said cell to said reservoir and to close said passageway in a second rotatable position, means covering said opened bottom of said cell body when a specimen is contained within said hollow.

2. The sample cup according to claim 1, wherein said extending peripheral flange of said cap member has a knurled outer side edge for ease in rotating.

3. The sample cup according to claim 1, wherein said cell body and cap member are fabricated from polyethylene.

4. The sample cup according to claim 1, wherein said aperture means of said first and said second flanges are rectangular in shape.

5. The sample cup according to claim 1, wherein said means covering said opened bottom of said cell body comprises a thin sheet of plastic stretched over said opened bottom, and an annular retaining ring position about an outer edge of said cell body near said opened bottom to hold said sheet in place.

6. The sample cup according to claim 5, wherein said thin plastic sheet is a polyester film.

7. The sample cup according to claim 1, wherein said cell body further includes a peripheral ridge located about an inner surface of said body and extending radially inwardly into said internal hollow.

8. The sample cup according to claim 7, wherein said peripherally disposed sidewall of said cap member includes a peripheral depression on an outer surface of said sidewall for coacting with said peripheral ridge of said cell body to enable rotation of said cap member with respect to said body.

9. The sample cup according to claim 1, wherein said cell body has a peripheral depression around an outer surface thereof and located nearer said opened bottom to coact with and retain an annular ring member.

10. The sample cup according to claim 9, wherein said annular ring member has an inwardly extending peripheral ridge about a top opening and adapted to coact with said depression in said cell body.

* * * * *